United States Patent
Fukuda

(10) Patent No.: US 10,575,718 B2
(45) Date of Patent: Mar. 3, 2020

(54) ENDOSCOPE SYSTEM

(71) Applicant: HOYA CORPORATION, Tokyo (JP)

(72) Inventor: Masaaki Fukuda, Tokyo (JP)

(73) Assignee: HOYA CORPORATION, Tokyo (JP)

(*) Notice: Subject to any disclaimer, the term of this patent is extended or adjusted under 35 U.S.C. 154(b) by 0 days.

(21) Appl. No.: 16/318,300

(22) PCT Filed: Sep. 1, 2017

(86) PCT No.: PCT/JP2017/031674
§ 371 (c)(1),
(2) Date: Jan. 16, 2019

(87) PCT Pub. No.: WO2018/043727
PCT Pub. Date: Mar. 8, 2018

(65) Prior Publication Data
US 2019/0223703 A1    Jul. 25, 2019

(30) Foreign Application Priority Data
Sep. 2, 2016  (JP) ................................. 2016-171951

(51) Int. Cl.
*A61B 1/045* (2006.01)
*A61B 1/00* (2006.01)
(Continued)

(52) U.S. Cl.
CPC ............ *A61B 1/045* (2013.01); *A61B 1/00* (2013.01); *A61B 1/0638* (2013.01); *A61B 1/0676* (2013.01); *G02B 23/2461* (2013.01)

(58) Field of Classification Search
CPC . A61B 5/1455; A61B 5/14551; A61B 5/0059; A61B 5/02416
See application file for complete search history.

(56) References Cited

U.S. PATENT DOCUMENTS 9,801,573 B2 * 10/2017 Saito .................. A61B 1/00009
2012/0253157 A1 * 10/2012 Yamaguchi .......... A61B 1/0638
600/328
(Continued)

FOREIGN PATENT DOCUMENTS

CN        102197983 A      9/2011
JP     2013-240401 A     12/2013
(Continued)

OTHER PUBLICATIONS

PCT/JP2017/031674 International Search Report, dated Nov. 14, 2017.
CN201780043153.6 Office Action, dated Jul. 30, 2019 (6 pp.).

*Primary Examiner* — Menatoallah Youssef
(74) *Attorney, Agent, or Firm* — Kilpatrick Townsend & Stockton LLP

(57) ABSTRACT

An endoscope system captures images of biological tissue when illuminated with first to third light, and generates first to third color image data. The amount of hemoglobin in the biological tissue and the oxygen saturation of the hemoglobin are calculated using components of the first to third color image data, an oxygen saturation distribution image that shows the distribution of the oxygen saturation is generated, and control is performed such that the generated oxygen saturation distribution image is displayed superimposed on a captured image of the biological tissue on a display. The oxygen saturation is calculated based on the amount of hemoglobin and a second ratio obtained using components of the color image data. The transparency is adjusted for pixels in which the value of the second ratio is outside an allowable range for the second ratio determined according to the amount of hemoglobin.

20 Claims, 8 Drawing Sheets

(51) Int. Cl.
    *A61B 1/06*         (2006.01)
    *G02B 23/24*      (2006.01)

(56)           References Cited

U.S. PATENT DOCUMENTS

| | | |
|---|---|---|
| 2015/0238127 A1 | 8/2015 | Saito |
| 2017/0098301 A1 | 4/2017 | Ikemoto et al. |

FOREIGN PATENT DOCUMENTS

| | | |
|---|---|---|
| JP | 2015-160013 A | 9/2015 |
| JP | 2015-198735 A | 11/2015 |
| WO | 2016/136698 A1 | 9/2016 |

\* cited by examiner

ENDOSCOPE SYSTEM

CROSS-REFERENCE TO RELATED APPLICATIONS

This application is a 371 U.S. National Phase of PCT International Application No. PCT/JP2017/031674 filed on Sep. 1, 2017, which claims benefit and priority to Japanese patent application No. 2016-171951 filed on Sep. 2, 2016, and which is incorporated by reference herein in its entirety.

TECHNICAL FIELD

The present disclosure relates to an endoscope system that performs image display of biological information in biological tissue based on image data generated by imaging the biological tissue.

BACKGROUND ART

An endoscope system has been known which includes a function of obtaining information on a biological substance in biological tissue, which is an imaging subject, such as information on an amount of hemoglobin and an oxygen saturation of hemoglobin, based on image data obtained by an endoscope, and performing image display. An example of this kind of endoscope system is disclosed in Patent Document 1.

The endoscope system disclosed in Patent Document 1 includes: an imaging means for obtaining spectral image data by capturing a spectroscopic image of a predetermined wavelength region in a body cavity; a processing means for performing predetermined processing on the spectral image data to generate composite image data in which a characteristic amount of the biological tissue, such as the oxygen saturation, is emphasized; and a display means for performing screen display based on the composite image data. The endoscope system can display the composite image as an image for specifying a lesioned part as distinguished from a healthy part.

CITATION LIST

Patent Documents

Patent Document 1: JP 2013-240401A

SUMMARY OF DISCLOSURE

Technical Problem

In the aforementioned endoscope system, the biological tissue is illuminated and imaged at a certain time interval using multiple types of light in different narrow wavelength bands in order to obtain spectral images, and therefore there are cases where positional shift occurs in the biological tissue image between the different spectral images due to movement of the biological tissue, shaking of the image sensor, and the like. As a result, in the generated composite image in which the distribution of a characteristic amount is emphasized, a disadvantageous problem occurs in which artifacts appear in the oxygen saturation distribution image, that is to say, a region showing an abnormal value for the oxygen saturation due to positional shifting of the biological tissue images is erroneously displayed as a region having a low oxygen saturation, or erroneously displayed as a region having a high oxygen saturation. This problem is not limited to spectral images, and can also occur when acquiring color image data for biological tissue that is constituted by color image data for the three colors R (red), G (green), and B (blue) by illuminating the biological tissue with multiple types of light that have different wavelength bands at a certain time interval.

The present disclosure has been made in view of the foregoing circumstance, and it is an object thereof to provide an endoscope system according to which, when displaying an oxygen saturation distribution image that indicates a distribution of the oxygen saturation of hemoglobin using biological tissue image data, it is possible to display an image that prevents the prominence of an abnormal value in the oxygen saturation distribution image caused by positional shift of biological tissue images.

Solution to the Problem

An endoscope system of the present disclosure has aspects such as the following.

Aspect 1

An endoscope system including:

a light source apparatus configured to emit at least two types of light with different wavelength bands;

an endoscope including an imaging unit that includes an image sensor configured to generate a plurality of pieces of color image data of images of biological tissue that correspond to the at least two types of light by imaging the biological tissue illuminated with the at least two types of light;

a processor including: a characteristic amount acquisition unit configured to calculate an amount of hemoglobin in the biological tissue and an oxygen saturation of the hemoglobin with use of a component of the color image data and generate an oxygen saturation distribution image that shows a distribution of the oxygen saturation, and an image display control unit configured to control a mode of displaying the oxygen saturation distribution image; and a display configured to display the oxygen saturation distribution image superimposed on an image of the biological tissue captured by the imaging unit, wherein the characteristic amount acquisition unit includes a hemoglobin amount calculation unit configured to calculate the amount of hemoglobin based on a first ratio obtained using a component of the color image data, and an oxygen saturation calculation unit configured to calculate an oxygen saturation of the hemoglobin based on the amount of hemoglobin and a second ratio obtained using a component of the color image data, and the image display control unit is configured to, for a pixel in which the value of the second ratio is outside an allowable range for the second ratio determined according to the amount of hemoglobin, adjust a transparency of the pixel that is to be superimposed on the image of the biological tissue.

Aspect 2

The endoscope system according to Aspect 1, wherein the light source apparatus is configured to emit at least three or more types of light including a first light in a first wavelength band, a second light in a second wavelength band that is different from the first wavelength band, and a third light in a third wavelength band that is different from the first wavelength band and the second wavelength band, the imaging unit is configured to generate first color image data corresponding to the first light, second color image data corresponding to the second light, and third color image data corresponding to the third light by imaging biological tissue illuminated with the first light, the second light, and the third light, the first ratio is a ratio between one component of the first color image data and one component of the second color image data, and the second ratio is a ratio between one component of the second color image data and one component of the third color image data.

Aspect 3

The endoscope system according to Aspect 2, wherein the first wavelength band is wider than the second wavelength band and the third wavelength band, and the second wavelength band is wider than the third wavelength band, and the first wavelength band includes a wavelength band according to which one component of the first color image data is not sensitive to change in the amount of hemoglobin of the biological tissue.

Aspect 4

The endoscope system according to Aspect 2 or 3, wherein the second wavelength band includes a wavelength band according to which one component of the second color image data is sensitive to change in the amount of hemoglobin of the biological tissue but is not sensitive to change in the oxygen saturation.

Aspect 5

The endoscope system according to any one of Aspects 2 to 4, wherein the first ratio is a ratio between a luminance component of the second color image data and an R component of the first color image data or a sum of the R component and a G component of the first color image data.

Aspect 6

The endoscope system according to any one of Aspects 2 to 5, wherein the second ratio is a ratio between a luminance component of the third color image data and a luminance component of the second color image data.

Aspect 7

The endoscope system according to any one of Aspects 2 to 6, wherein the second wavelength band is in a range of 500 nm to 600 nm, the third wavelength band is a wavelength band that is in the second wavelength band and is narrower than the second wavelength band, and the second light is filtered light obtained from the first light by using an optical filter to transmit a light component in the second wavelength band, and the third light is filtered light obtained from the first light by using an optical filter to transmit a light component in the third wavelength band.

Aspect 8

The endoscope system according to Aspect 1, wherein the light source apparatus is configured to emit first light that includes a light component in a fourth wavelength band and a light component in a fifth wavelength band that is different from the fourth wavelength band, and third light in a third wavelength band that is different from the fourth wavelength band and the fifth wavelength band, the imaging unit is configured to generate first color image data corresponding to the first light and third color image data corresponding to the third light by imaging the biological tissue illuminated with the first light and the third light, the first ratio is a ratio obtained from a ratio between corresponding components of the first color image data that correspond to the fourth wavelength band and the fifth wavelength band in the first color image data, and the second ratio is a ratio between one of the corresponding components and one component of the third color image data.

Aspect 9

The endoscope system according to Aspect 8, wherein the fifth wavelength band includes a wavelength band according to which, out of the corresponding components, a corresponding component that corresponds to the fifth wavelength band is sensitive to change in the amount of hemoglobin of the biological tissue but is not sensitive to change in the oxygen saturation.

Aspect 10

The endoscope system according to any one of Aspects 2 to 9, wherein the third wavelength band includes a wavelength band according to which one component of the third color image data is sensitive to change in the oxygen saturation.

Aspect 11

An endoscope system including:

a light source apparatus configured to emit light that includes at least three light components with different wavelength bands;

an endoscope including an imaging unit that includes an image sensor configured to generate color image data by imaging a biological tissue illuminated with the light;

a processor including: a characteristic amount acquisition unit configured to calculate an amount of hemoglobin and an oxygen saturation of the hemoglobin in the biological tissue with use of corresponding components of the color image data that correspond to the wavelength bands of the light components and generate an oxygen saturation distribution image that shows a distribution of the oxygen saturation, and an image display control unit configured to control a mode of displaying the oxygen saturation distribution image; and a display configured to display the oxygen saturation distribution image superimposed on an image of the biological tissue captured by the imaging unit, wherein the characteristic amount acquisition unit includes a hemoglobin amount calculation unit that calculates the amount of hemoglobin based on a first ratio obtained using the corresponding components, and a oxygen saturation calculation unit that calculates the oxygen saturation of the hemoglobin based on the amount of hemoglobin and a second ratio obtained using the corresponding components, and for a pixel in which the value of the second ratio is outside an allowable range for the second ratio determined according to the amount of hemoglobin, the image display control unit adjusts a transparency of the pixel that is to be superimposed on the image of the biological tissue.

Aspect 12

The endoscope system according to any one of Aspects 1 to 11, wherein the image display control unit sets the transparency of a pixel having a second ratio that is outside an allowable range higher than the transparency of a pixel having a second ratio that is in the allowable range.

Advantageous Effects of the Disclosure

According to the above-described endoscope system of the present disclosure, it is possible to display an oxygen saturation distribution image that prevents the prominence of abnormal values in the oxygen saturation distribution image that appear due to positional shift of biological tissue images.

DESCRIPTION OF EMBODIMENTS

Figure 1:
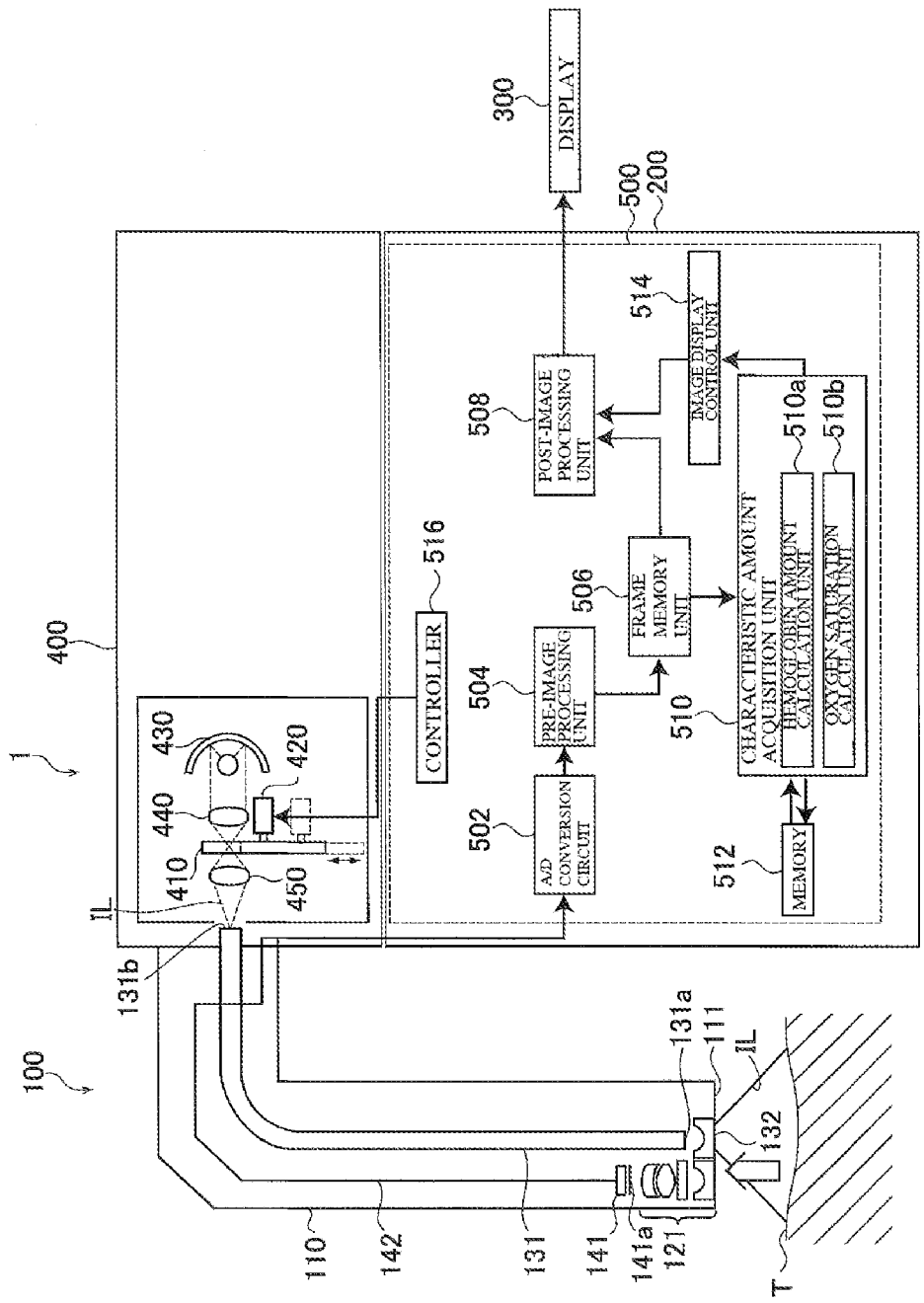
FIG. 1 is a block diagram showing a configuration of an example of an endoscope system of an embodiment.

An endoscope system of an embodiment described below is a system in which an amount of hemoglobin and an oxygen saturation of biological tissue are quantitatively calculated based on multiple pieces of color image data obtained by illuminating and imaging the biological tissue as an imaging subject with light having different wavelength bands, and an oxygen saturation distribution image is displayed. As will be described later, in another embodiment, there is no limitation to an embodiment in which multiple pieces of color image data are obtained by illuminating and imaging biological tissue with multiple types of light that have different wavelength bands. According to another embodiment, the amount of hemoglobin and the oxygen saturation of the biological tissue can be quantitatively calculated based on one piece of color image data obtained by illuminating and imaging the biological tissue with one type of light including a light component in a desired wavelength band, and an oxygen saturation distribution image can be displayed.

With the endoscope system of an embodiment of the present disclosure, biological tissue illuminated with at least two types of light that are emitted from a light source apparatus and have different wavelength bands is imaged by an image sensor, whereby the image sensor generates color image data for the image of the biological tissue corresponding to each type of light. A processor calculates the amount of hemoglobin and the oxygen saturation of the hemoglobin in the biological tissue using components of the generated color image data. Specifically, the processor calculates the amount of hemoglobin based on a later-described first ratio that is obtained using components of the color image data, also calculates the oxygen saturation of the hemoglobin based on the calculated amount of hemoglobin and a later-described second ratio that is obtained using components of the color image data, and generates an oxygen saturation distribution image that indicates the oxygen saturation distribution. Furthermore, the processor controls the display mode of the image such that the generated oxygen saturation distribution image is displayed superimposed on biological tissue images captured by the image sensor. In this control of the image display mode, in the case where the value of the second ratio of a pixel is outside an allowable range for the second ratio that is determined according to the amount of hemoglobin, the processor adjusts the transparency of that pixel according to which the pixel is displayed superimposed on the biological tissue images. In this way, the transparency (degree of transparency) is adjusted for pixels in the oxygen saturation distribution image that are outside the allowable range for the second ratio, thus making it possible to display an oxygen saturation distribution image that prevents the prominence of abnormal values in the oxygen saturation distribution image that occur due to positional shifting of the biological tissue images. Note that although the oxygen saturation is calculated based on the second ratio and the calculated amount of hemoglobin, given that the amount of hemoglobin is calculated based on the first ratio, the calculation of the oxygen saturation also includes being calculated based on the second ratio and the first ratio.

In the following, a pixel that is outside the allowable range and has a transparency adjusted to a value greater than 0% and less than or equal to 100% is called a transparent pixel. Accordingly, the term "transparent pixel" includes pixels having various degrees of transparency, from pixels that have a transparency of 100% and through which the biological tissue shown below is completely visible, to pixels that have a transparency of several percent and through which the biological tissue image shown below is only slightly visible.

Hereinafter, an embodiment of the present disclosure will be described with reference to the drawings.

Configuration of Endoscope System

FIG. 1 is a block diagram showing a configuration of an endoscope system 1 according to an embodiment. The endoscope system 1 includes: an electronic endoscope (endoscope) 100; a processor 200; a display 300; and a light source apparatus 400. The electronic endoscope 100 and the display 300 are detachably connected to the processor 200. The processor 200 includes an image processing unit 500. The light source apparatus 400 is detachably connected to the processor 200. The light source apparatus 400 may also be incorporated in the housing of the processor 200.

The electronic endoscope 100 includes an insertion tube 110 to be inserted into the body of an examinee. A light guide 131 that extends over approximately the entire length of the insertion tube 110 is provided inside of the insertion tube 110. A leading end portion 131a, which is one end portion of the light guide 131 is located near the leading end portion of the insertion tube 110, or in other words, near an insertion tube leading end portion 111, and a base end portion 131b, which is the other end portion of the light guide 131, is located at the portion at which the light guide 131 is connected to the light source apparatus 400. Accordingly, the light guide 131 extends from the portion at which the light guide 131 is connected to the light source apparatus 400 to near the insertion tube leading end portion 111.

The light source apparatus 400 includes, as a light source, a light source lamp 430 that generates light with a large light amount, such as a xenon lamp. The light emitted from the light source apparatus 400 is incident on the base end portion 131b of the light guide 131 as illuminating light IL. The light incident on the base end portion 131b of the light guide 131 is guided through the light guide 131 to the leading end portion 131a and is emitted from the leading end portion 131a. A light distribution lens 132 that is arranged facing the leading end portion 131a of the light guide 131 is provided at the insertion tube leading end portion 111 of the electronic endoscope 100. The illuminating light IL emitted from the leading end portion 131a of the light guide 131 passes through the light distribution lens 132 and illuminates biological tissue T near the insertion tube leading end portion 111.

An object lens group 121 and an image sensor 141 are provided at the insertion tube leading end portion 111 of the electronic endoscope 100. The object lens group 121 and the image sensor 141 form an imaging unit. The light reflected or dispersed by the surface of the biological tissue T in the illuminated light IL is incident on the object lens group 121, is condensed, and forms an image on a light receiving surface of the image sensor 141. As the image sensor 141, it is possible to use a known image sensor, such as a CCD (Charge Coupled Device) image sensor or a CMOS (Complementary Metal Oxide Semiconductor) image sensor for color image imaging, with a light receiving surface provided with a color filter 141a.

Figure 2:
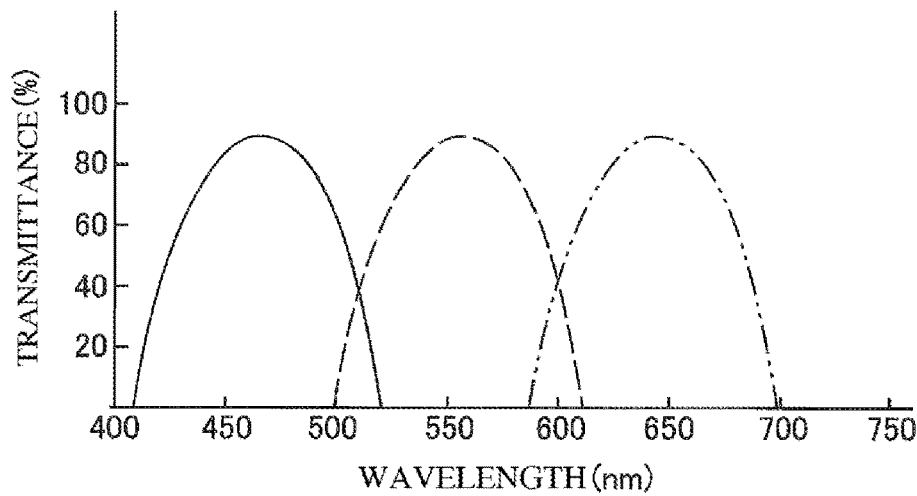
FIG. 2 is a diagram showing an example of spectral characteristics of red (R), green (G), and blue (B) filters of an image sensor used in an embodiment.

The color filter 141a is a so-called on-chip filter in which R color filters that allow transmission of red-colored light, G color filters that allow transmission of green-colored light, and B color filters that allow transmission of blue-colored light are arrayed and formed directly on the light-receiving elements of the image capture element 141. FIG. 2 is a diagram showing an example of spectral characteristics of red (R), green (G), and blue (B) filters of an image sensor used in an embodiment. The R color filter is a filter that allows transmission of light with a wavelength longer than a wavelength of about 570 nm (e.g., 580 nm to 700 nm), the G color filter is a filter that allows transmission of light with a wavelength of about 470 nm to 620 nm, and the B color filter is a filter that allows transmission of light with a wavelength shorter than a wavelength of about 530 nm (e.g., 420 nm to 520 nm).

The image sensor 141 is an imaging means for imaging the biological tissue T illuminated with the multiple types of light and generating color image data corresponding to the types of light, and is an image data generation means for generating color image data corresponding to the light reflected by or dispersed on the biological tissue T due to the biological tissue T being illuminated with multiple types of light with different wavelength ranges. The image sensor 141 is controlled so as to perform driving in synchronization with the image processing unit 500, which will be described later, and periodically (e.g., in intervals of 1/30 of a second) outputs the color image data corresponding to the image of the biological tissue T formed on the light receiving surface. The color image data output from the image sensor 141 is sent to the image processing unit 500 of the processor 200 via a cable 142.

The image processing unit 500 mainly includes: an A/D conversion circuit 502; a pre-image processing unit 504; a frame memory unit 506; a post-image processing unit 508; a characteristic amount acquisition unit 510; a memory 512; an image display control unit 514; and a controller 516.

The A/D conversion circuit 502 performs A/D conversion on the color image data input via the cable 142 from the image sensor 141 of the electronic endoscope 100 and outputs digital data. The digital data output from the A/D conversion circuit 502 is sent to the pre-image processing unit 504.

The pre-image processing unit 504 uses the digital data to generate color image data composed of R, G, and B components that form an image, or components in desired wavelength bands, through demosaic processing from R digital image data imaged by the light receiving elements in the image sensor 141 on which the R color filters are mounted, G digital image data imaged by the light receiving elements in the image sensor 141 on which the G color filters are mounted, and B digital image data imaged by the light receiving elements in the image sensor 141 on which the B color filters are mounted. Furthermore, the pre-image processing unit 504 is a portion that implements predetermined signal processing such as color correction, matrix operation, and white balance correction on the generated R, G, and B color image data.

The frame memory unit 506 temporarily stores color image data of each image that was imaged by the image sensor 141 and subjected to signal processing.

The post-image processing unit 508 generates screen data for display on a display by reading out the color image data stored in the frame memory unit 506 or performing signal processing (γcorrection, etc.) on the image data generated by a later-described image display control unit 514. As will be described later, the image data generated by the image display control unit 514 includes image data of a distribution of a characteristic amount such as the oxygen saturation of hemoglobin in the biological tissue T. The generated image data (video format signal) is output to the display 300. Accordingly, an image of the biological tissue T, the characteristic amount distribution image of the biological tissue T, and the like are displayed on the screen of the display 300.

As will be described later, in response to an instruction from a controller 516, the characteristic amount acquisition unit 510 calculates the amount of hemoglobin and the oxygen saturation of the hemoglobin in the imaged biological tissue T as characteristic amounts, and generates image data of a distribution of the characteristic amounts for display on the captured image of the biological tissue T.

The characteristic amount acquisition unit 510 calculates the characteristic amounts by performing calculation using the color image data of the biological tissue T, which was illuminated with multiple types of light in different wavelength bands, and therefore the color image data and various types of information to be used by the characteristic amount acquisition unit 510 are called from the frame memory unit 506 or the memory 512.

In accordance with an instruction from the controller 516, the image display control unit 514 controls the display mode of the distribution image of the characteristic amounts calculated by the characteristic amount acquisition unit 510. The image display control unit 514 performs control such that an image of a distribution of the oxygen saturation of the hemoglobin (a oxygen saturation distribution image) is displayed superimposed on the captured image of the biological tissue T.

The controller 516 is a portion that, in addition to performing operation instruction and operation control for the portions of the image processing unit 500, performs operation instruction and operation control of the portions of the electronic endoscope 100 including the light source apparatus 400 and the image sensor 141.

Note that the characteristic amount acquisition unit 510 and the image display control unit 514 may be constituted by a software module that carries out the above-described functions by starting up and executing a program in a computer, and may be constituted by hardware.

In this manner, the processor 200 includes both a function of processing the color image data output from the image sensor 141 of the electronic endoscope 100 and a function of instructing and controlling operation of the electronic endoscope 100, the light source apparatus 400, and the display 300.

According to one embodiment of the light source apparatus 400, the light source apparatus 400 is a light emitting means for emitting a first light, a second light, and a third light, and causes the first light, the second light, and the third light to be incident on the light guide 131. The light source apparatus 400 emits the first light, the second light, and the third light, which have different wavelength bands, but the light source apparatus 400 may also emit one or two types of light, and may also emit four or more types of light. In the case of emitting four or more types of light, the fourth light may be a light with the same wavelength band as the first light. In addition to the light source lamp 430, the light source apparatus 400 includes: a light condensing lens 440; a rotating filter 410; a filter control unit 420; and a light condensing lens 450. The light, which is approximately parallel light and is emitted from the light source lamp 430, is white light, for example, and is condensed by the light condensing lens 440, passes through the rotating filter 410, and thereafter is once again condensed by the light condensing lens 450 and is incident on the base end 131*b* of the light guide 131. Note that the rotating filter 410 can move between a position on the light path of the light irradiated from the light source lamp 430 to a retracted position off of the light path due to a moving mechanism (not shown), such as a linear guideway. Since the rotating filter 410 includes multiple filters with different transmission characteristics, the wavelength band of the light emitted from the light source apparatus 400 differs depending on the type of the rotating filter 410 that crosses the light path of the light irradiated from the light source lamp 430.

Note that the configuration of the light source apparatus 400 is not limited to that shown in FIG. 1. For example, a lamp that generates convergent light instead of parallel light may also be employed as the light source lamp 430. In this case, for example, a configuration may be used in which the light irradiated from the light source lamp 430 is condensed in front of the condensing lens 440 and the light is incident on the light condensing lens 440 as diffused light. Also, a configuration may be used in which the light condensing lens 440 is not used and approximately parallel light generated by the light source lamp 430 is directly incident on the rotating filter 410. Also, in the case of using a lamp that generates convergent light, a configuration may be used in which a collimator lens is used instead of the light condensing lens 440 and the light is incident on the rotating filter 410 in an approximately parallel state. For example, in the case of using an interference-type optical filter such as a multi-layered dielectric filter as the rotating filter 410, the approximately parallel light is incident on the rotating filter 410, whereby the incidence angle of the light on the optical filter is made uniform, and thus a more preferable filter characteristic can be obtained. Also, a lamp that generates diffused light may also be employed as the light source lamp 430. In this case as well, a configuration can be used in which a collimator lens is used instead of the light condensing lens 440 and the light is incident on the rotating filter 410 in an approximately parallel state.

Also, although the light source apparatus 400 is configured to emit multiple types of light with different wavelength bands by causing the light irradiated from the one light source lamp 430 to pass through the optical filter, a semiconductor light source such as a light-emitting diode or a laser element that outputs laser light, for example, can also be used as a light source apparatus 400, instead of the light source lamp 43. In this case, the rotating filter 410 need not be used. Also, for example, the light source apparatus 400 can also be configured to separately emit white light including excitation light with a predetermined wavelength band and fluorescent light that is excited to emit light by the excitation light, and light with a predetermined narrow wavelength band.

The configuration of the light source apparatus 400 is not particularly limited, as long as multiple types of light with different wavelength bands are emitted.

Although the light source apparatus 400 is an external apparatus attached to the electronic endoscope 100, if the light source apparatus 400 is constituted by a small light source such as a laser element, the light source apparatus 400 may be provided on the insertion tube leading end portion 111 of the electronic endoscope 100. In this case, the need for the light guide 131 is eliminated.

The rotating filter 410 is a circular disk-shaped optical unit including multiple optical filters, and is configured such that the transmission wavelength region is switched according to the rotation angle. The rotating filter 410 includes three optical filters with different transmission wavelength bands, but the rotating filter 410 may include four, five, six, or more optical filters. The rotation angle of the rotating filter 410 is controlled by the filter control unit 420 connected to the controller 516. Due to the controller 516 controlling the rotation angle of the rotating filter 410 via the filter control unit 420, the wavelength band of the illuminating light IL supplied to the light guide 131 is switched by passing through the rotating filter 410.

Figure 3:
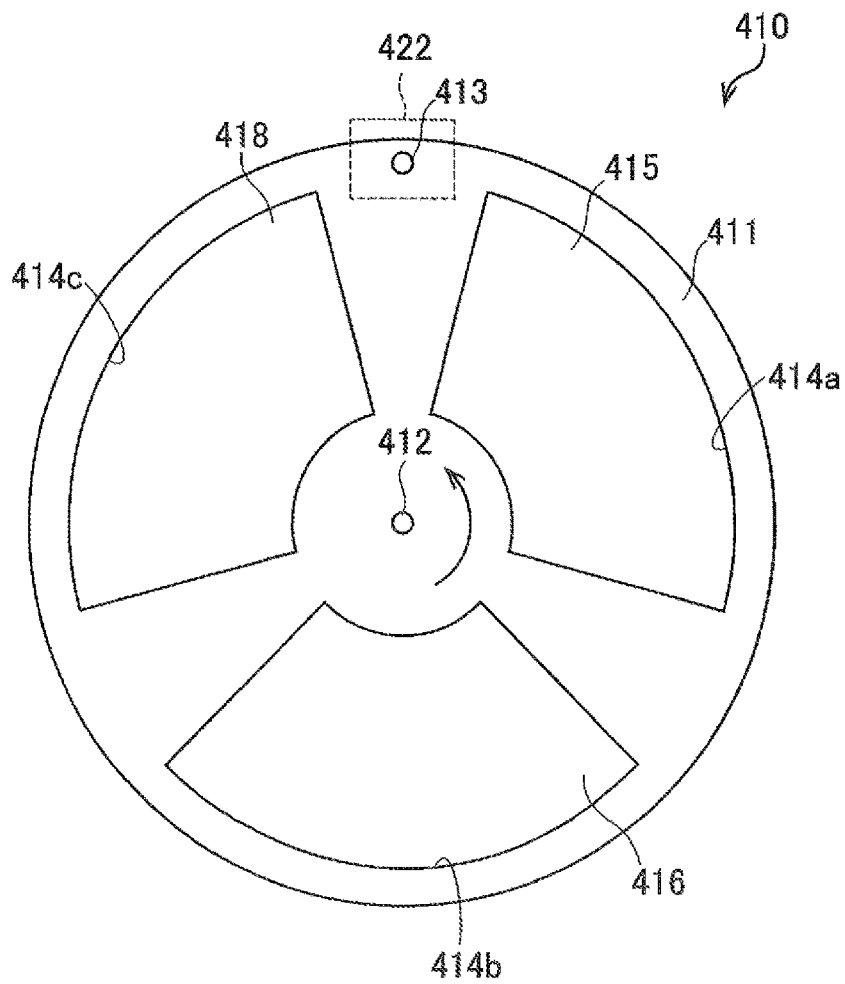
FIG. 3 is an external view (front view) of a rotating filter to be used in a light source apparatus of an embodiment.

FIG. 3 is an external view (front view) of the rotating filter 410. The rotating filter 410 includes: an approximately circular disk-shaped frame 411; and three fan-shaped optical filters 415, 416, and 418. Three fan-shaped windows 414*a*, 414*b*, and 414*c* are formed at an equal interval around the central axis of the frame 411, and the optical filters 415, 416, and 418 are fit into the respective windows 414*a*, 414*b*, and 414*c*. Note that the optical filters in this embodiment are all multilayered dielectric filters, but another type of optical filter (e.g., an absorption-type optical filter or an etalon filter in which a dielectric multilayer film is used as a reflection film, etc.) may also be used.

Also, a boss hole 412 is formed on the central axis of the frame 411. An output shaft of a servo motor (not shown) included in the filter control unit 420 is fixed by being inserted into the boss hole 412 and the rotating filter 410 rotates along with the output shaft of the servo motor.

When the rotating filter 410 rotates in the direction indicated by the arrow in FIG. 3, the optical filters on which the light is incident switch in the following order: optical filters 415, 416, and 418, and thereby the wavelength bands of the illuminating light IL passing through the rotating filter are sequentially switched.

Figure 4:
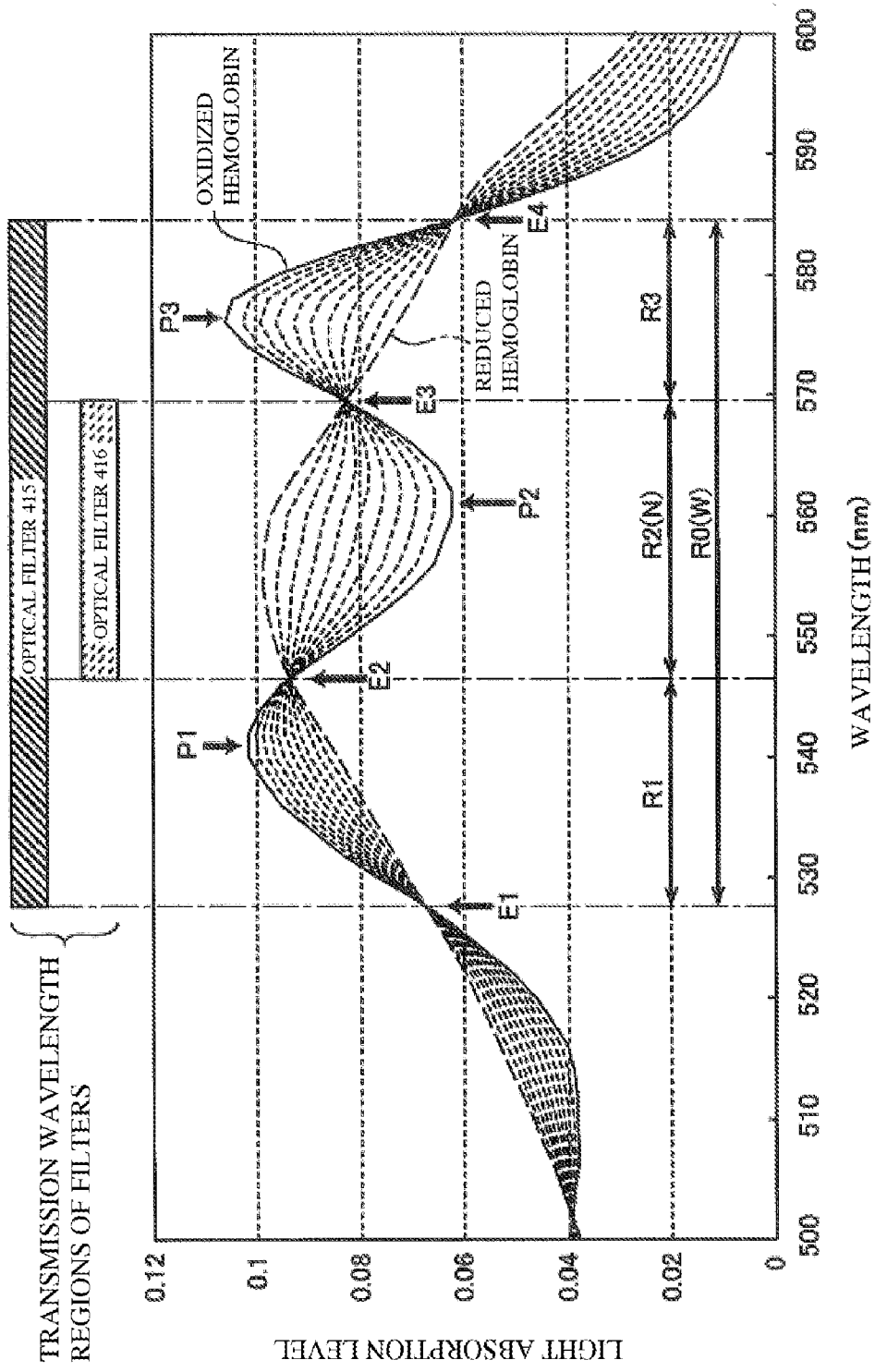
FIG. 4 is a diagram showing an example of an absorption spectrum of hemoglobin near 550 nm.

The optical filters 415 and 416 are optical band-pass filters that selectively allow transmission of light in the 550-nm band. As shown in FIG. 4, the optical filter 415 is configured to allow transmission with low loss of light in a wavelength band R0 (W band) from the isosbestic points E1 to E4, and to block light of other wavelength regions. Also, the optical filter 416 is configured to allow transmission with low loss of light in the wavelength band R2 (N band) from the isosbestic point E2 to the isosbestic point E3, and to block light of other wavelength regions.

Also, the optical filter 418 is an ultraviolet-cutting filter, and in the visible light wavelength region, the light emitted from the light source lamp 430 passes through the optical filter 418. The light that has passed through the optical filter 418 is used as white light WL to capture a normal observation image. Note that it is also possible to use a configuration in which the optical filter 418 is not used and the window 414c of the frame 411 is open.

Accordingly, the light that has passed through the optical filter 415 among the light irradiated from the light source lamp 430 is referred to hereinafter as "wide light", the light that has passed through the optical filter 416 among the light irradiated from the light source lamp 430 is referred to hereinafter as "narrow light", and light that has passed through the optical filter 418 among the light irradiated from the light source lamp 430 is referred to hereinafter as "white light WL".

As shown in FIG. 4, the wavelength band R1 is a band in which the peak wavelength of an absorption peak P1 originating from oxidized hemoglobin is included, the wavelength band R2 is a band in which the peak wavelength of an absorption peak P2 originating from reduced hemoglobin is included, and the wavelength band R3 is a band in which the peak wavelength of an absorption peak P3 originating from oxidized hemoglobin is included. Also, the peak wavelengths of the three absorption peaks P1, P2, and P3 are included in the wavelength region R0. Note that FIG. 4 is a diagram showing an example of an absorption spectrum of hemoglobin near 550 nm.

Also, the wavelength band R0 of the optical filter 415 and the wavelength band R2 of the optical filter 416 are included in the transmission wavelength region (FIG. 2) of the G color filter of the color filter 141a. Accordingly, images of the biological tissue T formed by light that has passed through the optical filters 415 and 416 are obtained as images of the G component of the color image data captured by the image sensor 141. Note that the transmittance and aperture of the optical filter 415 or the optical filter 418 are adjusted such that light intensity of the wide light generated by the optical 415 and the light intensity of the while light WL generated by the optical filter 418 are approximately the same. The light intensity of the wide light and the light intensity of the narrow light are different from each other.

A through hole 413 is formed on the circumferential edge portion of the frame 411. The through hole 413 is formed at the same position (phase) as the boundary portion between the window 414a and the window 414c in the rotation direction of the frame 411. A photointerrupter 422 for detecting the through hole 413 is arranged on the periphery of the frame 411 so as to surround part of the circumferential edge portion of the frame 411. The photointerrupter 422 is connected to the filter control unit 420.

Thus, it is preferable to have a configuration in which the light source apparatus 400 emits types of light with different wavelength bands, that is, the wide light, the narrow light, and the white light WL, as the illuminating light IL by sequentially switching the multiple optical filters 415, 416, and 418 on the light path of the light irradiated by the light source lamp 430.

Calculation of Characteristic Amount of Biological Tissue

A characteristic amount of the biological tissue T is calculated by the characteristic amount acquisition unit 510 of the processor 500. Processing for calculating the amount of hemoglobin and the oxygen saturation Sat of the hemoglobin in the biological tissue T as the characteristic amounts from a captured image of the biological tissue T will be described below.

As shown in FIG. 4, hemoglobin has strong absorption bands called Q bands, which originate from porphyrin, near 550 nm. The absorption spectrum of hemoglobin changes according to the oxygen saturation Sat, which indicates the percentage of oxidized hemoglobin HbO in all of the hemoglobin. The waveform with the solid line in FIG. 4 is the absorption spectrum of an oxygen saturation Sat of 100%, that is, oxidized hemoglobin, and the waveform with the long broken line is the absorption spectrum of an oxygen saturation Sat of 0%, that is, reduced hemoglobin Hb. Also, the short broken lines are the absorption spectra of hemoglobin with intermediate oxygen saturations Sat of 10%, 20%, 30%, . . . and 90%, that is, a mixture of oxidized hemoglobin HbO and reduced hemoglobin Hb.

As shown in FIG. 4, in the Q band, the oxidized hemoglobin HbO and the reduced hemoglobin Hb have mutually different peak wavelengths. Specifically, the oxidized hemoglobin HbO has an absorption peak P1 near the wavelength 542 nm and an absorption peak P3 near the wavelength 576 nm. On the other hand, the reduced hemoglobin Hb has an absorption peak P2 near 556 nm. Since FIG. 4 shows absorption spectra in the case where the sum of the concentrations of the oxidized hemoglobin HbO and the reduced hemoglobin Hb is constant, isosbestic points E1, E2, E3, and E4, at which the light absorption degree is constant regardless of the proportion of the oxidized hemoglobin HbO and the reduced hemoglobin Hb, that is, regardless of the oxygen saturation, appear. In the following description, the wavelength band interposed between the isosbestic points E1 and E2 is the wavelength band R1, which was described above for the optical filter 410, the wavelength band interposed between the isosbestic points E2 and E3 is the wavelength band R2, the wavelength band interposed between the isosbestic points E3 and E4 is the wavelength band R3, and the wavelength band interposed between the isosbestic points E1 and E4, that is, the band obtained by combining the wavelength bands R1, R2, and R3, is the wavelength band R0. Accordingly, the wavelength band of the wide light, which is the transmission light that passed through the optical filter 415 among the light irradiated from the light source lamp 430, is the wavelength band R0, and the wavelength band of the narrow light, which is the transmission light that passed through the optical filter 416 among the light irradiated from the light source lamp 430, is the wavelength band R2.

As shown in FIG. 4, in the wavelength bands R1, R2, and R3, the absorption of the hemoglobin increases or decreases linearly with respect to the oxygen saturation. Specifically, absorptions AR1 and AR3 of the hemoglobin in the wavelength bands R1 and R3 linearly increase with respect to the concentration of the oxidized hemoglobin, that is, the oxygen saturation. Also, the absorption AR2 of the hemoglobin in the wavelength band R2 increases linearly with respect to the concentration of the reduced hemoglobin.

Here, the oxygen saturation is defined using the following equation (1).

Equation (1):

$$Sat = \frac{[HbO]}{[Hb]+[HbO]}$$ Equation 1 where
Sat: oxygen saturation
[Hb]: Concentration of reduced hemoglobin
[HbO]: Concentration of oxidized hemoglobin
[Hb]+[HbO]: Amount of hemoglobin (tHb)

Also, equation (2) and equation (3), which indicate the concentrations of the oxidized hemoglobin HbO and the reduced hemoglobin Hb, are obtained using equation (1).

Equation (2):

$$[HbO]=Sat \cdot ([Hb]+[HbO])$$ Equation 2

Equation (3):

$$[Hb]=(1-Sat) \cdot ([Hb]+[HbO])$$ Equation 3

Accordingly, the absorptions AR1, AR2, and AR3 of the hemoglobin are characteristic amounts that depend on both the oxygen saturation and the amount of hemoglobin.

Here, it is evident that the total value of the light absorption level in the wavelength band R0 is a value that does not depend on the oxygen saturation Sat and is determined by the amount of hemoglobin. Accordingly, the amount of hemoglobin can be quantified based on the total value of the light absorption level in the wavelength band R0. Also, the oxygen saturation Sat can be quantified based on the total value of the light absorption levels in the wavelength band R1, the wavelength band R2, or the wavelength band R3, and the amount of hemoglobin quantified based on the total value of the wavelength band R0.

The characteristic amount acquisition unit 510 includes: a hemoglobin amount calculation unit 510a that calculates and acquires the amount of hemoglobin (first characteristic amount) in the biological tissue T based on a later-described first ratio that is sensitive to change in the amount of hemoglobin in the biological tissue T; and an oxygen saturation calculation unit 510b that calculates and acquires the oxygen saturation (second characteristic amount) of the hemoglobin in the biological tissue T based on the calculated amount of hemoglobin (first characteristic amount) and a later-described second ratio that is sensitive to change in the oxygen saturation of the hemoglobin. The first ratio and the second ratio being sensitive to change in the amount of hemoglobin or change in the oxygen saturation means that the first ratio and the second ratio change with respect to change in the amount of hemoglobin or change in the oxygen saturation.

Due to the fact that the value of the luminance component of the color image data of the biological tissue T illuminated with the wide light (the light in the wavelength band R0 that passed through the optical filter 415) corresponds to the total value of the light absorption levels in the above-described wavelength band R0, the hemoglobin amount calculation unit 510a of the characteristic amount acquisition unit 510 calculates the amount of hemoglobin based on the luminance component of the color image data in the wavelength band R0. Here, the luminance component can be calculated by multiplying a predetermined coefficient by the R component of the color image data, multiplying a predetermined coefficient by the G component of the color image data, multiplying a predetermined coefficient by the value of the B component of the color image data, and adding together the multiplication results.

Specifically, the hemoglobin amount calculation unit 510a of the characteristic amount acquisition unit 510 calculates the amount of hemoglobin based on a ratio Wide(Yh)/WL(R) or Wide(Yh)/{WL(R)+WL(G)} (first ratio) obtained by dividing the luminance component Wide (Yh) of the color image data (second color image data) of the biological tissue T in which the wide light (second light) is used as the illuminating light IL, by an R component WL(R) or a total component WL(R)+WL(G) of the R component WL(R) and a G component WL(G) of the color image data (first color image data) of the biological tissue T in which the white light WL (first light) is used as the illuminating light IL. The ratio Wide(Yh)/WL(R) or Wide(Yh)/{WL(R)+WL(G)} obtained by dividing the luminance component Wide (Yh) by WL(R) or {WL(R)+WL(G)} is used in the calculation of the amount of hemoglobin in order to cancel out changes in the spectral characteristic of the biological tissue T according to the degree to which the illuminating light IL is diffused by the surface of the biological tissue T. In particular, the reflection spectrum of biological tissue T of the inner wall of a digestive organ or the like is easily influenced by the wavelength property of the diffusion of the illuminating light by the biological tissue T, in addition to the wavelength property (specifically, the absorption spectrum property of the oxidized hemoglobin and the reduced hemoglobin) of the absorption by the components constituting the biological tissue T. The R component WL(R) or the total component WL(R)+WL(G) of the R component and the G component of the color image data (first color image data) of the biological tissue T in which the white light WL (first light) is used as the illuminating light IL is not influenced by the amount of hemoglobin and the oxygen saturation Sat and indicates the degree of diffusion of the biological tissue T of the illuminating light IL. Accordingly, in order to cancel out the influence of the diffusion of the biological tissue T of the illuminating IL from the reflection spectrum of the biological tissue T, the wavelength band of the white light WL (reference light) is preferably set such that one component of the first color image data includes a wavelength band that is not sensitive to changes in the amount of hemoglobin in the biological tissue T. In addition to this, the wavelength band of the white light WL (reference light) is preferably set such that one component of the first color image data includes a wavelength band that is not sensitive to the changing of the oxygen saturation.

In an embodiment, a reference table, which indicates the correlation between information of the above-described first ratio and the amount of hemoglobin in the biological tissue with a known amount of hemoglobin, is stored in the memory 512 in advance, and the hemoglobin amount calculation unit 510a of the characteristic amount acquisition unit 510 uses the reference table to calculate the amount of hemoglobin based on the above-described first ratio in the color image data obtained by imaging the biological tissue T.

In the calculation of the amount of hemoglobin of an embodiment, it is preferable to use, as the first ratio, a ratio Wide(Yh)/WL(R) or Wide(Yh)/{WL(R)+WL(G)} of the luminance component Wide(Yh) of the color image data (second color image data) of the biological tissue T in which the wide light (second light) is used as the illuminating IL and the R component WL(R) or the total components WL(R)+WL(G) of the R component and the G component of the color image data (first color image data) of the biological tissue T in which the white light WL (first light) is used as the illuminating IL, but it is also preferable to use the G component Wide(G) instead of the luminance component Wide(Yh) of the color image data (second color image data) of the biological tissue T in which the wide light (second light) is used as the illuminating IL.

Furthermore, as described above, due to the fact that the total value of the light absorption level in the wavelength band R2 decreases along with an increase in the oxygen saturation Sat, and that the total value of the light absorption level in the wavelength band R0 changes according to the amount of hemoglobin but is constant regardless of changes in the oxygen saturation Sat, the oxygen saturation calculation unit 510b of the characteristic amount acquisition unit 510 calculates the oxygen saturation based on the second ratio determined below. That is, the oxygen saturation calculation unit 510b of the characteristic amount acquisition unit 510 calculates, as the second ratio, a ratio Narrow(Yh)/Wide(Yh) of the luminance component Narrow(Yh) of the color image data (third color image data) of the biological tissue illuminated with the narrow light, which is the light in the wavelength band R2 that passed through the optical filter 416, and the luminance component Wide(Yh) of the color image data (second color image data) of the biological tissue T illuminated with the wide light (the light in the wavelength band R0 that passed through the optical filter 416). On the other hand, a correlation indicating the relationship between the amount of hemoglobin, the lower limit value of the second ratio at which the oxygen saturation Sat=0%, and the upper limit value of the second ratio Narrow(Yh)/Wide(Yh) at which the oxygen saturation Sat=100% is obtained from a known sample and stored in advance in the memory 512. The oxygen saturation calculation unit 510b of the characteristic amount acquisition unit 510 obtains the lower limit value and the upper limit value of the second ratio using the above-described correlation and the calculation result of the amount of hemoglobin obtained from the color image data generated by imaging the biological tissue T. Furthermore, the oxygen saturation calculation unit 510b calculates the position in the range between the upper limit value and the lower limit value in which the value of the second ratio Narrow(Yh)/Wide(Yh) of the imaged biological tissue T is located, using the fact that the oxygen saturation Sat changes linearly according to the second ratio between the obtained lower limit value and upper limit value. In this manner, the oxygen saturation calculation unit 510b of the characteristic amount acquisition unit 510 calculates the oxygen saturation Sat.

Also, according to an embodiment, a reference table indicating the amount of hemoglobin and the correlation between the value of the second ratio and the oxygen saturation Sat of the hemoglobin is obtained from a known sample and stored in advance in the memory 512, and the oxygen saturation Sat of the hemoglobin can also be calculated based on the calculated second ratio by referencing the reference table.

In one embodiment, the second ratio is used as a ratio between the luminance component Narrow(Yh) of the color image data (third color image data) of the biological tissue T illuminated with the narrow light and the luminance component Wide(Yh) of the color image data (second color image data) of the biological tissue T illuminated with the wide light, but it is also possible to use the ratio between the G component Narrow(G) of the color image data (third color image data) of the biological tissue T illuminated with the narrow light and the G component Wide(G) of the color image data (second color image data) of the biological tissue T illuminated with the wide light.

Also, in an embodiment, in order to calculate the second ratio, the narrow light in the wavelength band R2 is used to illuminate the biological tissue T, but there is no limitation to the narrow light. For example, it is also possible to use light whose wavelength band is the wavelength band R1 or the wavelength band R2, with the intention of using the wavelength band R1 or the wavelength band R2 in which the total value of the light absorption level changes with respect to change in the oxygen saturation Sat. In this case, the filter characteristic of the optical filter 416 is preferably set to the wavelength band R1 or the wavelength band R2.

Thus, in an embodiment, it is preferable that the wavelength band of the narrow light (third light) is included in the wavelength band of the wide light (second light) in order to accurately calculate the oxygen saturation Sat. Also, in light of the fact that the oxygen saturation Sat can be calculated accurately, the wavelength band of the wide light (second light) is preferably set such that one component of the second color image data, such as the luminance component or G component, includes the wavelength band R0, which is sensitive to change in the amount of hemoglobin but is not sensitive to change in the oxygen saturation. In light of the fact that the oxygen saturation Sat can be calculated accurately, the wavelength band of the narrow light (third light) is set such that one component of the third color data, such as the luminance component or the G component, includes the wavelength band R2, which is sensitive to change in the oxygen saturation Sat of the biological tissue T.

Also, in light of the fact that the influence of the spectral property of the diffused light on the biological tissue T can be canceled out, the wavelength band of the white light WL (first light) is preferably set such that one component of the first color image data includes a wavelength band that is not sensitive to change in the amount of hemoglobin of the biological tissue T.

Also, it is preferable that the above-described wide light (second light) is filtered white light WL (first light) obtained by allowing the first wavelength band in the region from 500 nm to 600 nm, for example, the wavelength band between the isosbestic point E1 and the isosbestic point E4, in the wavelength band of the white light WL (first light) to pass through one optical filter, and the narrow light (third light) is filtered light of the white light WL (first light) obtained by allowing a second wavelength band that is narrower than the first wavelength band in the range of the first wavelength band, such as the wavelength band between the isosbestic point E2 and the isosbestic point E3, to pass through one optical filter. For example, the first wavelength band is preferably a band in the range of 510 nm to 590 nm. Also, for example, the second wavelength band is preferably a band in the region of 510 nm to 590 nm, and is more preferably a band in the region of 530 nm to 580 nm.

Also, in the above-described embodiment, when the light absorption level of the hemoglobin is used to calculate the hemoglobin amount and the oxygen saturation, the light in the wavelength band near 550 nm is used as illuminating light, but this is an example. In the light absorption level of the hemoglobin, outside of the wavelength band near 550 nm, a large absorption peak exists at 420 to 450 nm and includes isosbestic points. In the periphery of the isosbestic points, the waveforms of the absorption spectra of the oxidized hemoglobin and the reduced hemoglobin are alternatingly switched. For this reason, in an embodiment, it is also preferable that the hemoglobin amount and the oxygen saturation are calculated using light with different wavelengths or wavelength bands in the wavelength band of 400 to 460 nm as the illuminating light. In this case as well, the hemoglobin amount and the oxygen saturation are calculated as described below.

Figure 5:
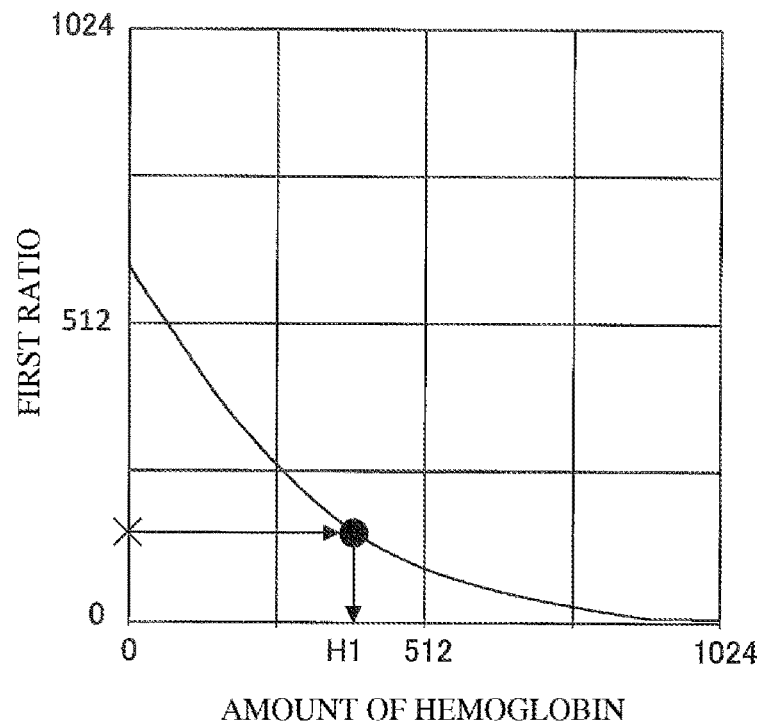
FIG. 5 is a diagram showing an example of a relationship between a first ratio and an amount of hemoglobin, which is used in an embodiment.

FIG. 5 is a diagram showing an example of a relationship between a first ratio and an amount of hemoglobin. When the first ratio is obtained as described above, the hemoglobin amount calculation unit 510a of the characteristic amount acquisition unit 510 references the reference table showing the relationship shown in FIG. 5 and obtains the amount of hemoglobin based on the obtained first ratio. FIG. 5 indicates that the hemoglobin amount H1 is obtained based on the value of the first ratio. The numerical values on the horizontal axis and the vertical axis of FIG. 5 are conveniently denoted as the values 0 to 1024.

Figure 6:
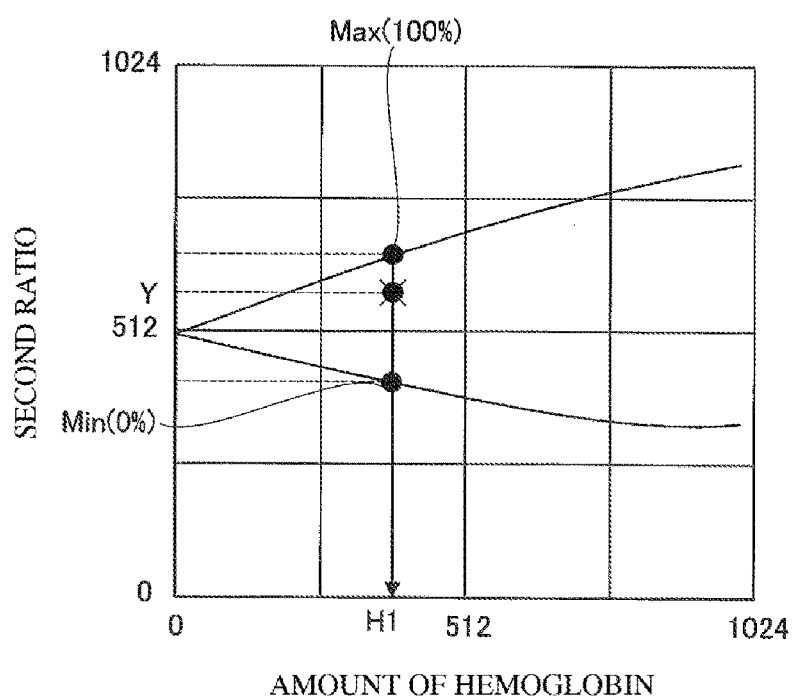
FIG. 6 is a diagram showing an example of a relationship between an upper limit value and a lower limit value of a second ratio and an amount of hemoglobin, which is used in an embodiment.

FIG. 6 is a diagram showing an example of a relationship between the upper limit value and lower limit value of the second ratio and the amount of hemoglobin. The numerical values on the horizontal axis and the vertical axis of FIG. 6 are conveniently denoted as the values 0 to 1024.

When the second ratio is obtained as described above, the oxygen saturation amount calculation unit 510b of the characteristic amount acquisition unit 510 uses the correlation shown in FIG. 6 to obtain the upper limit value and the lower limit value of the second ratio in the obtained amount of hemoglobin, based on the second ratio and the amount of hemoglobin obtained by the hemoglobin amount calculation unit 510a. The upper limit value indicates that the oxygen saturation Sat=100%, and the lower limit value indicates that the oxygen saturation Sat=0%. By determining the position between the upper limit value and the lower limit value at which the obtained second ratio is located, the oxygen saturation amount calculation unit 510b obtains the value of the oxygen saturation Sat. Assuming that the oxygen saturation varies linearly accordingly the value of the second ratio when between 0 and 100%, the value of the oxygen saturation is calculated based on the value of the second ratio. In FIG. 6, the upper limit value Max (100%) and the lower limit value Min (0%) when the value of the hemoglobin is H1 is obtained. The value of the oxygen saturation Sat is obtained based on the upper limit value Max (100%), the lower limit value Min (0%), and the value Y of the second ratio.

The oxygen saturation Sat obtained in this manner is obtained for each pixel of the image of the biological tissue T, and therefore the distribution of the oxygen saturation Sat on the image of the biological tissue T can be shown as an oxygen saturation distribution image. The oxygen saturation distribution image is indicated by a gradation in which the color of the pixels is changed (e.g., changed from red to blue) according to the values of the oxygen saturation Sat of the pixels.

Display of Oxygen Saturation Distribution Image

As described above, in the endoscope system 1, the oxygen saturation Sat of the hemoglobin is calculated based on a ratio (second ratio) obtained from the components of color image data that corresponds to different types of light and was generated by illuminating and imaging the biological tissue T using multiple types of light, and therefore the oxygen saturation distribution image that uses color gradation to display the distribution of the oxygen saturation Sat according to the values of the oxygen saturation Sat is also an image that reflects positional shift of the biological tissue T image in the captured images.

More specifically, the calculation of the oxygen saturation Sat is performed by calculating the amount of hemoglobin based on the first ratio, and calculating the oxygen saturation Sat based on the second ratio and the amount of hemoglobin. Here, the first ratio and the second ratio are ratios of components of color image data generated by imaging the biological tissue T that is illuminated with white light WL, wide light, and narrow light, which have different wavelength bands, at a certain time interval. There are cases where the image of the biological tissue T in these captured images shifts between different images due to movement of the biological tissue, camera shake of the image sensor, and the like. For example, there are cases where the image of the biological tissue T corresponding to the white light WL and the image of the biological tissue corresponding to the wide light are shifted in an image, cases where the image of the biological tissue T corresponding to the wide light and the image of the biological tissue corresponding to the narrow light are shifted in an image, and cases where the image of the biological tissue T corresponding to the white light WL, the image of the biological tissue corresponding to the wide light, and the image of the biological tissue corresponding to the narrow light are shifted from each other in an image, for example.

Figure 7A:
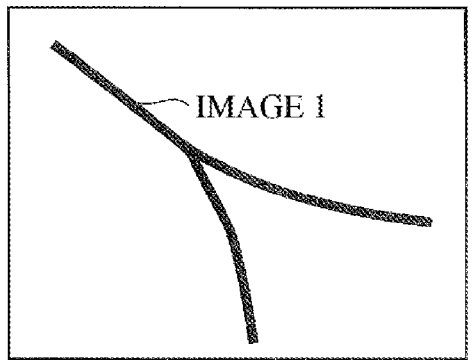
FIGS. 7(a) to 7(c) are diagrams illustrating positional shifting of biological tissue images captured through illumination with different types of light.
Figure 7B:
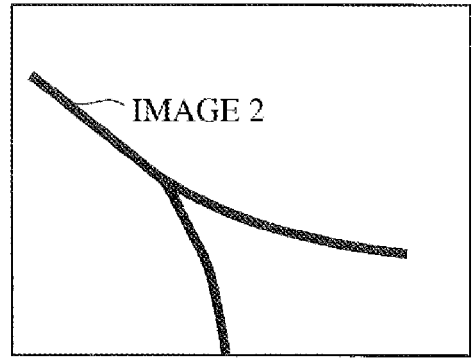
Figure 7C:
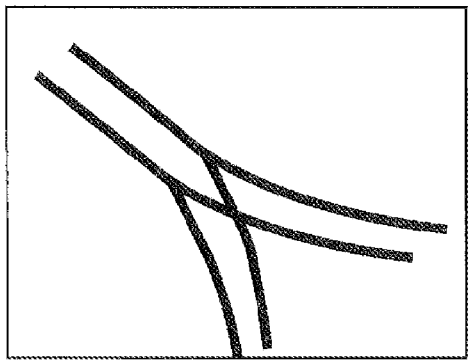

FIGS. 7(a) to 7(c) are diagrams illustrating positional shifting of biological tissue images captured through illumination with different types of light. FIGS. 7(a) to 7(c) respectively show an image 1 of the biological tissue T captured when illuminated with the white light WL, an image 2 that is an image of the biological tissue T captured when illuminated with the wide light and that is shifted from the image 1, and a distribution image 3 of the amount of hemoglobin obtained from image data of the image 1 and the image 2.

The image 2 is shifted downward and leftward in the image relative to the image 1. The value of the first ratio obtained from the image data of the image 1 and the image 2 is higher or lower at a position that is not related to the original image due to positional shift. For this reason, due to positional shift, locations with a high amount of hemoglobin and locations with a low amount of hemoglobin are formed as artifacts in the distribution image of the amount of hemoglobin that is obtained based on the first ratio, as shown in FIG. 7(c).

FIGS. 8(a) to 8(d) are diagrams illustrating positional shifting of biological tissue images captured through illumination with different types of light. FIGS. 8(a) to 8(d) respectively show an image 3 of the biological tissue T captured when illuminated with the white light WL, an image 4 that is an image of the biological tissue T captured when illuminated with the wide light and that is shifted from the image 3, an image 5 that is an image of the biological tissue T captured when illuminated with the narrow light and that is shifted from the image 3 and the image 4, and a distribution image 6 of the amount of hemoglobin obtained from the image data of the images 3 to 5.

The image 4 is not shifted from the image 3, and therefore artifacts caused by positional shift are not formed in the distribution image of the amount of hemoglobin. However, the image 5 is shifted downward and leftward in the image relative to the image 4. The value of the second ratio obtained from the image data of the image 4 and the image 5 is higher or lower at a position that is not related to the original image due to positional shift. For this reason, locations with a high oxygen saturation (solid black portions) and locations with a low oxygen saturation (white portions) are formed as artifacts in the hemoglobin oxygen saturation distribution image (Sat distribution image) that is obtained based on the second ratio and the distribution image of the amount of hemoglobin that does not have artifacts, as shown in FIG. 8(d).

Figure 9:
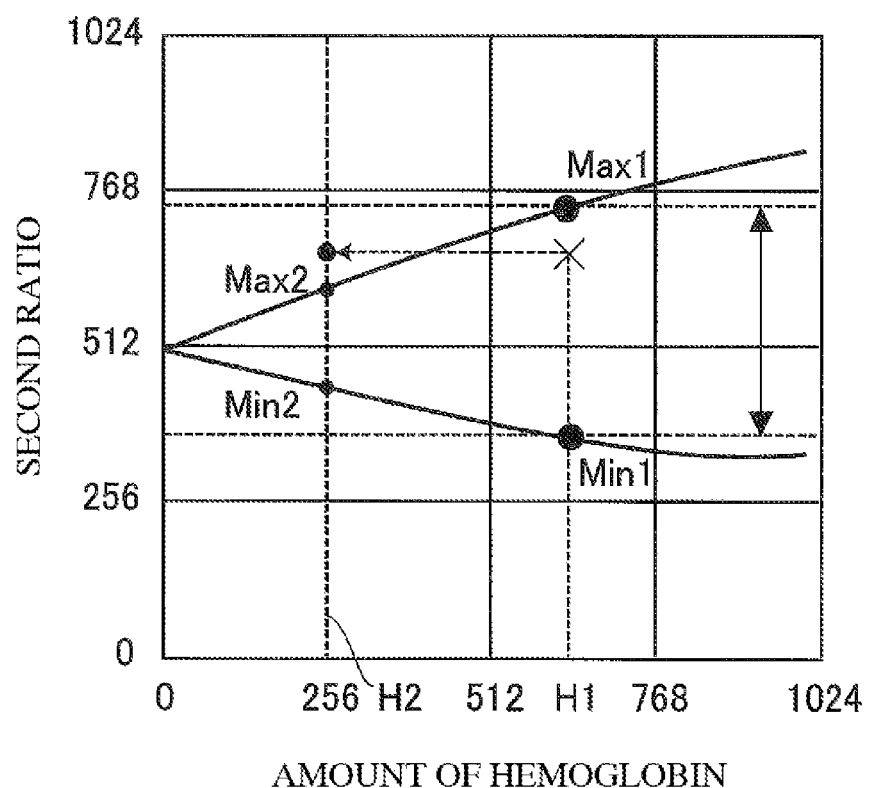
FIG. 9 is a diagram illustrating the formation of an oxygen saturation Sat artifact that appears due to positional shifting of biological tissue images captured by an imaging unit.

FIG. 9 is a diagram illustrating the formation of oxygen saturation Sat artifacts that appear due to image positional shift. The numerical values on the horizontal axis and the vertical axis of FIG. 9 are denoted as the values 0 to 1024 for convenience. There are cases where even though the amount of hemoglobin is originally a value H1, a value H2 lower than the value H1 is obtained as the amount of hemoglobin as shown in FIG. 9 due to the distribution image of the amount of hemoglobin shown in FIG. 7(c) that is formed due to positional shift of the image 1 and the image 2 as shown in FIGS. 7(a) and 7(b). In this case, even if there is no positional shift between the image of the biological tissue T captured when illuminated with the wide light and the image of the biological tissue T captured when illuminated with the narrow light, the upper limit value and the lower limit value of the second ratio decrease from Max1 and Min1 to Max2 and Min2. For this reason, there are cases where the second ratio is outside the range between the upper limit value Max2 and the lower limit value Min2 as shown in FIG. 9, and, for example, red is used for display if the second ratio exceeds the upper limit value Max2, and blue is used for display if the second ratio falls below the lower limit value Min2. For this reason, there are cases where red or blue artifacts appear in the oxygen concentration distribution image in which the value of the oxygen saturation Sat is displayed using various colors, as shown in FIG. 7(c).

Figure 8A:
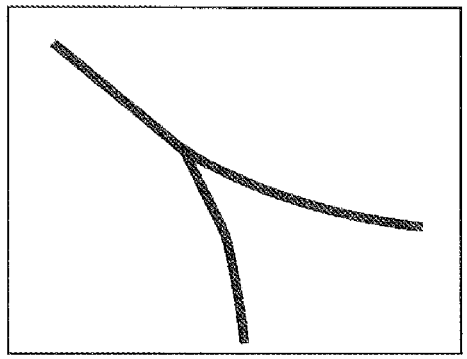
FIGS. 8(a) to 8(d) are diagrams illustrating positional shifting of biological tissue images captured through illumination with different types of light.
Figure 8B:
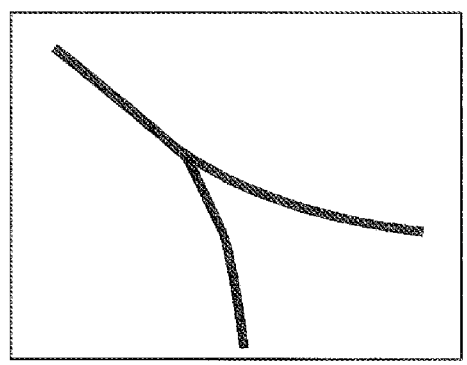
Figure 8C:
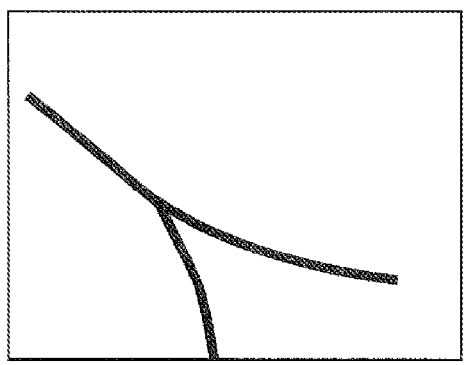
Figure 8D:
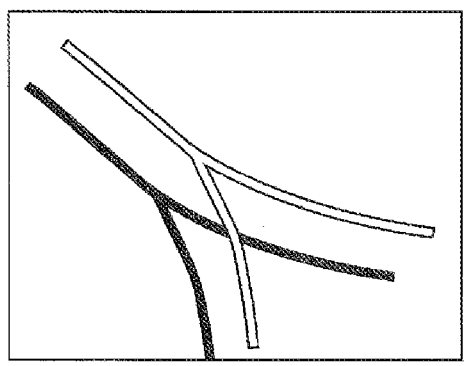

Also, even if a correct distribution image of the amount of hemoglobin is obtained because the image 3 and the image 4 are not shifted from each other as shown in FIGS. 8(a) to (c), due to the fact that the image 4 and the image 5 are shifted from each other, the second ratio obtained based on the image data of the image 4 and the image 5 will be high in some locations and low in some locations due to the positional shift. In this case, even if the value of the amount of hemoglobin is the correct original value H1, there are cases where the second ratio is outside the range between the upper limit value Max1 and the lower limit value Min1, and for example, red is used for display if the second ratio exceeds the upper limit value Max1, and blue is used for display if the second ratio falls below the lower limit value Min1. For this reason, red or blue artifacts appear in the oxygen concentration distribution image in which the value of the oxygen saturation Sat is displayed using various colors, as shown in FIG. 8(d).

In order to suppress the appearance of such artifacts, in one embodiment, the transparency is adjusted for pixels in the oxygen saturation distribution image for which the value of the second ratio is outside an allowable range for the second ratio that is determined according to the amount of hemoglobin, that is to say, outside the range between the upper limit value and the lower limit value. Specifically, the image display control unit 514 controls the image data such that the oxygen saturation distribution image is displayed superimposed on the image of the biological tissue T. At this time, the image display control unit 514 adjusts the transparency for pixels in the oxygen saturation distribution image for which the value of the second ratio is outside the allowable range for the second ratio that is determined according to the amount of hemoglobin, that is to say, outside the range between the upper limit value and the lower limit value. Specifically, the image display control unit 514 sets the transparency of a pixel that is outside of the allowable range for the second ratio higher than the transparency of a pixel that is inside the allowable range for the second ratio. For example, a pixel having a second ratio that is inside the allowable range is a non-transparent pixel having a transparency of 0, and a pixel having a second ratio that is outside the allowable range is set as a transparent pixel. As described above, the term "transparent pixel" includes pixels having a transparency that is greater than 0% and less than or equal to 100%. In the above embodiment, all pixels having a second ratio that is outside the allowable range for the second ratio are set as pixels having a transparency of 100% for example, but adjustment can also be performed such that the transparency is gradually changed, such as the transparency gradually increasing along with an increase in the difference between the value of the second ratio and the upper limit value or lower limit value of the second ratio.

Figure 10A:
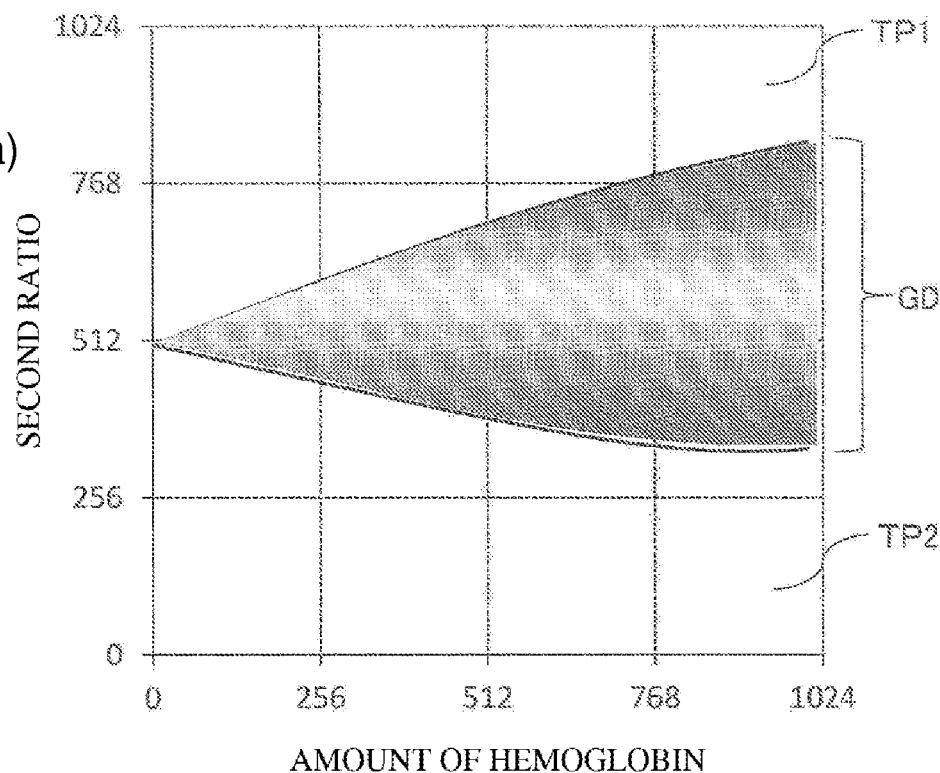
FIG. 10(a) is a diagram illustrating an example of adjustment of the transparency of pixels in an embodiment.
Figure 10B:
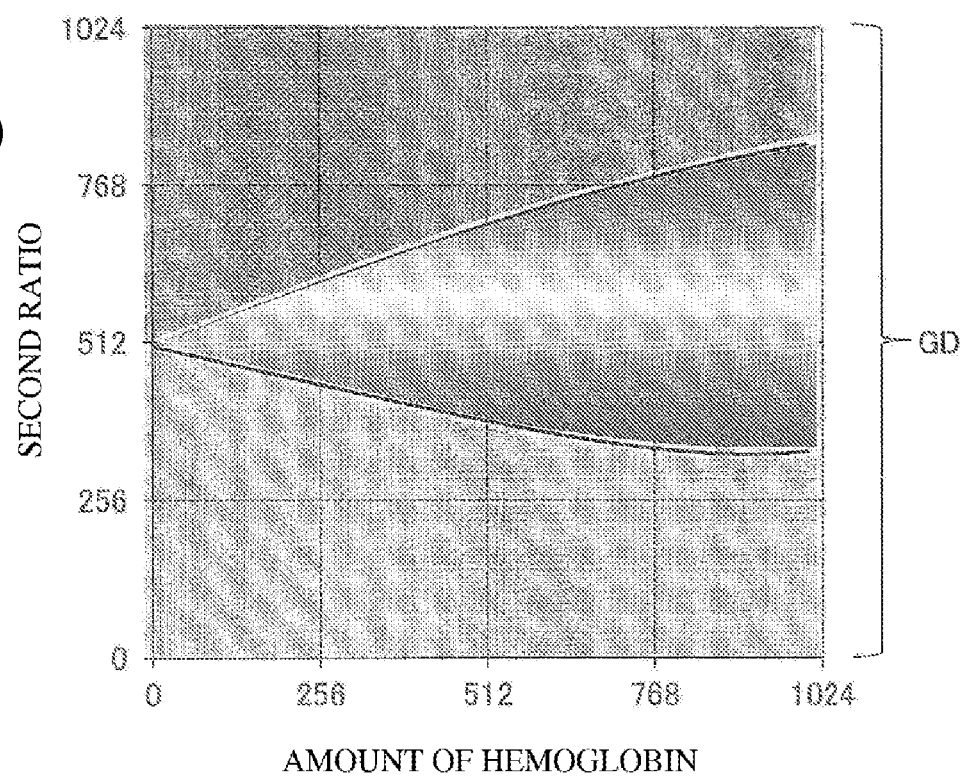
FIG. 10(b) illustrates conventional pixel gradation.

FIG. 10(a) is a diagram illustrating an example of adjustment of the transparency of pixels in an embodiment, and FIG. 10(b) illustrates conventional pixel gradation setting.

A region in which the second ratio, which is determined according to the amount of hemoglobin, is between the upper limit value and the lower limit value is assumed to be a gradation region GD in which the color is changed according to the oxygen saturation Sat, and a region in which the second ratio exceeds the upper limit value and a region in which the second ratio falls below the lower limit value are assumed to be transparent pixel regions TP1 and TP2. In conventional gradation, as shown in FIG. 10(b), regions in which the second ratio is outside the range between the upper limit value and the lower limit value are also gradation regions GD in which red and blue are used for display.

In this way, by setting pixels in the oxygen saturation distribution image that are outside the allowable range for the second ratio as transparent pixels, the image of the biological tissue T can be seen through such pixels, thus making it possible to display an oxygen saturation distribution image that prevents the prominence of abnormal values and artifacts caused by image positional shift. For this reason, when the operator using this endoscope system judges whether or not there is a malignant tumor portion and specify the location thereof based on a region having a low oxygen saturation in a body cavity, it is possible to reduce the likelihood of making an erroneous judgment and specifying an erroneous location.

In the above embodiment, three types of light having different wavelength bands are used as the illuminating when obtaining the amount of hemoglobin and the oxygen saturation Sat. However, according to an embodiment, it is also preferable that, in order to obtain the amount of hemoglobin and the oxygen saturation Sat, the light source apparatus 400 emits types of illuminating including first light that includes a light component in a fourth wavelength band and a light component in a fifth wavelength band that is different from the fourth wavelength band, and third light in a third wavelength band that is different from the fourth wavelength band and the fifth wavelength band. In this case, it is preferable that the hemoglobin amount calculation unit 510a calculates the amount of hemoglobin based on the first ratio obtained from the ratio of the component a and the component b that are corresponding components that correspond to the fourth wavelength band and the fifth wavelength band and are extracted from first color image data generated when the first light is used as the illuminating, and that the oxygen saturation calculation unit 510b generates the second ratio based on one of the component a and the component b and one component (component in the third wavelength band) of third color image data generated when the third light is used as the illuminating, and calculates the oxygen saturation Sat of the hemoglobin based on the second ratio and the amount of hemoglobin calculated by the hemoglobin amount calculation unit 510*a*. The corresponding components that correspond to the wavelength bands of the two light components and are extracted from the first color image data can be extracted by a matrix computation in the image processing unit 504 (corresponding component extraction unit) in the processor 200 shown in FIG. 1.

At this time, according to an embodiment, the fifth wavelength band includes a wavelength band according to which the corresponding component that corresponds to the fifth wavelength band in the first color image data is sensitive to change in the amount of hemoglobin in biological tissue but is not sensitive to change in the oxygen saturation, and this is preferable due to being able to calculate a precise amount of hemoglobin.

At this time, the third wavelength band includes a wavelength band according to which one component of the third color image data is sensitive to change in the oxygen saturation, and this is preferable due to being able to calculate a precise oxygen saturation.

For example, the first light includes a light component in the fourth wavelength band of 620 to 670 nm (red component), and a light component in the fifth wavelength band of 525 582 nm (green component). The third wavelength band of the second light is 545 to 570 nm. In this case, according to an embodiment, the first ratio, which is an index for obtaining the amount of hemoglobin, can be the ratio of the corresponding component corresponding to the green light component (component in the wavelength band of 525 to 582 nm) to the sum of the corresponding component that corresponds to the green light component (component in the wavelength band of 525 to 582 nm) and the corresponding component that corresponds to the red light component (component in the wavelength band of 620 to 670 nm), that is to say a composite corresponding component, and furthermore, the second ratio, which is an index for obtaining the oxygen saturation Sat, can be the ratio of the component that corresponds to the wavelength band of 545 to 570 nm in the third color image data to the corresponding component that corresponds to the green light component in the first color image data (component in the wavelength band of 525 to 582 nm).

Also, according to an embodiment, it is also possible to obtain the amount of hemoglobin and the oxygen saturation Sat using the components of color image data obtained using, as the illuminating, one type of light that has three light components instead of three types of light. In this case, one type of light is used as the illuminating light, and therefore since the configuration of the light source apparatus 400 is simplified and there is no need to generate the multiple pieces of color image data, the configuration of the portions of the processor 200 is simplified. Furthermore, the endoscope 100 only performs image capturing using illuminating emitted one time, and therefore there are no abnormal values in the oxygen saturation distribution image that appear due to positional shift of images of the biological tissue that occurs when image capturing is performed multiple times as described above. However, there are cases where the color image data includes noise components, and cases where camera shake occurs in the image of the biological tissue when performing image capturing one time, and artifacts may appear in the oxygen saturation distribution image. For this reason, it is preferable that, for pixels for which the value of the second ratio is outside the allowable range for the second ratio that is determined according to the amount of hemoglobin, the image display control unit 514 adjusts the transparency at which those pixels are superimposed on the image of the biological tissue.

In this case, the hemoglobin amount calculation unit 510*a* calculates the amount of hemoglobin based on the first ratio that is obtained using corresponding component that correspond to the wavelength bands of three color components extracted from the color image data, and the oxygen saturation calculation unit 510*b* calculates the oxygen saturation of the hemoglobin based on the second ratio, which is obtained using the extracted corresponding components, and the calculated amount of hemoglobin or the first ratio.

In this case, for example, it is preferable that the light component (blue light component) of the wavelength band of 450 to 500 nm, the light component (green light component) of the wavelength band of 525 to 582 nm, and the light component (red light component) of the wavelength band of 620 to 670 nm are included in the one type of light. The three corresponding components of the color image data that correspond to the above-described wavelength bands can be obtained due to the color image data obtained with this kind of light being subjected to a matrix operation by the pre-image processing unit 504 shown in FIG. 1. In this case, according to an embodiment, the first ratio, which is an index for obtaining the amount of hemoglobin, can be the ratio of the corresponding component that corresponds to the green light component (component in the wavelength band of 525 to 582 nm) with respect to the composite corresponding component obtained from the three corresponding components (e.g., a corresponding component having a value obtained by finding a weighted average of the values of the three corresponding components). Furthermore, the second ratio, which is an index for obtaining the oxygen saturation Sat, can be the ratio of the corresponding component that corresponds to the blue light component (component in the wavelength band of 450 to 500 nm) with respect to the corresponding component that corresponds to the green light component (component in the wavelength band of 525 to 582 nm). That is, the light source apparatus 400 is configured to emit a first light including three light components with different wavelength bands. The pre-image processing unit 504 (corresponding component extraction unit) of the processor 200 extracts the corresponding component of the first color image data that corresponds to each wavelength band of the light components from the first color image data generated in this manner by the electronic endoscope 100. Using the extracted corresponding components, the characteristic amount acquisition unit 510 acquires the amount of hemoglobin and the oxygen saturation Sat as characteristic amounts of the biological tissue.

In order to perform highly-accurate diagnosis in the endoscope system 1, it is required that the oxygen saturation distribution image indicating the distribution of the oxygen saturation Sat has high image quality. For this reason, the oxygen saturation distribution image preferably has 1 million pixels or more, more preferably 2 million pixels or more, and even more preferably 8 million pixels or more. On the other hand, the greater the number of pixels in the image being handled is, the larger the arithmetic circuit of the processor 200 tends to be, and the greater the processing load also tends to be. In particular, with a high number of pixels (high image quality) of 1 million pixels or more, the above-described tendency is prominent. In the embodiment described above, a reference table in which the amount of hemoglobin, the oxygen saturation Sat, and the color image data is associated, and information on the correlation are obtained in advance, and the amount of hemoglobin and the oxygen saturation Sat are calculated using the reference table and the correlation, and therefore in the above-described embodiment, the amount of hemoglobin and the oxygen saturation Sat can be calculated efficiently compared to the case of calculating the amount of hemoglobin and the oxygen saturation each time the color image data is acquired and without using the reference table and the correlation. For this reason, the arithmetic circuit of the processor 200 can be made smaller, and thus a processor 200 with a low cost, low heat generation, and low power consumption can be provided even if an image with high image quality is to be generated.

Although an embodiment is described above, the present disclosure is not limited to the above-described configuration, and various modifications are possible within the range of the technical idea of the present disclosure.

REFERENCE SIGNS LIST

1 Endoscope system
100 Electronic endoscope
110 Insertion tube
111 Insertion tube leading end portion
121 Object lens group
131 Light guide
131a Leading end portion
131b Base end portion
132 Lens
141 Image sensor
141a Color filter
142 Cable
200 Processor
300 Display
400 Light source unit
410 Rotating filter
420 Filter control unit
430 Light source lamp
440 Light condensing lens
450 Light condensing lens
500 Image processing unit
502 A/D conversion circuit
504 Pre-image processing unit
506 Frame memory unit
508 Post-image processing unit
510 Characteristic amount acquisition unit
512 Memory
514 Image display control unit
516 Controller

The invention claimed is:

1. An endoscope system comprising:
a light source apparatus configured to emit at least two types of light with different wavelength bands;
an endoscope including an imaging unit that includes an image sensor configured to generate a plurality of pieces of color image data of images of biological tissue that correspond to the at least two types of light by imaging the biological tissue illuminated with the at least two types of light;
a processor including: a characteristic amount acquisition unit configured to calculate, with use of a component of the color image data, an amount of hemoglobin in the biological tissue and an oxygen saturation of the hemoglobin and to generate an oxygen saturation distribution image that shows a distribution of the oxygen saturation, and an image display control unit configured to control a mode of displaying the oxygen saturation distribution image; and
a display configured to display the oxygen saturation distribution image superimposed on an image of the biological tissue captured by the imaging unit,
wherein the characteristic amount acquisition unit includes a hemoglobin amount calculation unit configured to calculate the amount of hemoglobin based on a first ratio obtained using a component of the color image data, and an oxygen saturation calculation unit configured to calculate an oxygen saturation of the hemoglobin based on the amount of hemoglobin and a second ratio obtained using a component of the color image data, and
the image display control unit is configured to, for a pixel in which the value of the second ratio is outside an allowable range for the second ratio determined according to the amount of hemoglobin, adjust a transparency of the pixel that is to be superimposed on the image of the biological tissue.

2. The endoscope system apparatus according to claim 1, wherein the light source apparatus is configured to emit at least three or more types of light including a first light in a first wavelength band, a second light in a second wavelength band that is different from the first wavelength band, and a third light in a third wavelength band that is different from the first wavelength band and the second wavelength band,
the imaging unit is configured to generate first color image data corresponding to the first light, second color image data corresponding to the second light, and third color image data corresponding to the third light by imaging biological tissue illuminated with the first light, the second light, and the third light,
the first ratio is a ratio between one component of the first color image data and one component of the second color image data, and
the second ratio is a ratio between one component of the second color image data and one component of the third color image data.

3. The endoscope system according to claim 2, wherein the first wavelength band is wider than the second wavelength band and the third wavelength band, and the second wavelength band is wider than the third wavelength band, and
the first wavelength band includes a wavelength band according to which one component of the first color image data is not sensitive to change in the amount of hemoglobin of the biological tissue.

4. The endoscope system according to claim 2, wherein the second wavelength band includes a wavelength band according to which one component of the second color image data is sensitive to change in the amount of hemoglobin of the biological tissue but is not sensitive to change in the oxygen saturation.

5. The endoscope system according to claim 2, wherein the first ratio is a ratio between a luminance component of the second color image data and an R component of the first color image data or is a ratio between the luminance component of the second color image data and a sum of the R component and a G component of the first color image data.

6. The endoscope system according to claim 2, wherein the second ratio is a ratio between a luminance component of the third color image data and a luminance component of the second color image data.

7. The endoscope system according to claim 2,
wherein the second wavelength band is in a range of 500 nm to 600 nm,
the third wavelength band is a wavelength band that is in the second wavelength band and is narrower than the second wavelength band, and
the second light is filtered light obtained from the first light by using an optical filter to transmit a light component in the second wavelength band, and the third light is filtered light obtained from the first light by using an optical filter to transmit a light component in the third wavelength band.

8. The endoscope system according to claim 1,
wherein the light source apparatus is configured to emit first light that includes a light component in a fourth wavelength band and a light component in a fifth wavelength band that is different from the fourth wavelength band, and third light in a third wavelength band that is different from the fourth wavelength band and the fifth wavelength band,
the imaging unit is configured to generate first color image data corresponding to the first light and third color image data corresponding to the third light by imaging the biological tissue illuminated with the first light and the third light,
the first ratio is a ratio obtained from a ratio between corresponding components of the first color image data that correspond to the fourth wavelength band and the fifth wavelength band in the first color image data, and
the second ratio is a ratio between one of the corresponding components and one component of the third color image data.

9. The endoscope system according to claim 8,
wherein the fifth wavelength band includes a wavelength band according to which, out of the corresponding components, a corresponding component that corresponds to the fifth wavelength band is sensitive to change in the amount of hemoglobin of the biological tissue but is not sensitive to change in the oxygen saturation.

10. The endoscope system according to claim 2,
wherein the third wavelength band includes a wavelength band according to which one component of the third color image data is sensitive to change in the oxygen saturation.

11. The endoscope system according to claim 1,
wherein the image display control unit sets the transparency of a pixel having a second ratio that is outside an allowable range to be higher than the transparency of a pixel having a second ratio that is in the allowable range.

12. An endoscope system comprising:
a light source apparatus configured to emit light that includes at least three light components with different wavelength bands;
an endoscope including an imaging unit that includes an image sensor configured to generate color image data by imaging a biological tissue illuminated with the light;
a processor including: a characteristic amount acquisition unit configured to calculate, with use of corresponding components of the color image data that correspond to the wavelength bands of the light components, an amount of hemoglobin and an oxygen saturation of the hemoglobin in the biological tissue and to generate an oxygen saturation distribution image that shows a distribution of the oxygen saturation, and an image display control unit configured to control a mode of displaying the oxygen saturation distribution image; and
a display configured to display the oxygen saturation distribution image superimposed on an image of the biological tissue captured by the imaging unit,
wherein the characteristic amount acquisition unit includes a hemoglobin amount calculation unit that calculates the amount of hemoglobin based on a first ratio obtained using the corresponding components, and a oxygen saturation calculation unit that calculates the oxygen saturation of the hemoglobin based on the amount of hemoglobin and a second ratio obtained using the corresponding components, and
for a pixel in which the value of the second ratio is outside an allowable range for the second ratio determined according to the amount of hemoglobin, the image display control unit adjusts a transparency of the pixel that is to be superimposed on the image of the biological tissue.

13. A method of analyzing biological tissue comprising:
emitting at least two types of light with different wavelength bands;
generating a plurality of pieces of color image data of images of biological tissue that correspond to the at least two types of light by imaging the biological tissue illuminated with the at least two types of light;
with use of a component of the color image data, calculating an amount of hemoglobin in the biological tissue and an oxygen saturation of the hemoglobin;
generating an oxygen saturation distribution image that shows a distribution of the oxygen saturation;
controlling a mode of displaying the oxygen saturation distribution image; and
displaying the oxygen saturation distribution image superimposed on an image of the biological tissue captured by the imaging,
wherein the calculating an amount of hemoglobin is based on a first ratio obtained using a component of the color image data, and
wherein the calculating an oxygen saturation of the hemoglobin is based on the amount of hemoglobin and a second ratio obtained using a component of the color image data, and
wherein the controlling a mode comprises, for a pixel in which the value of the second ratio is outside an allowable range for the second ratio determined according to the amount of hemoglobin, adjusting a transparency of the pixel that is to be superimposed on the image of the biological tissue.

14. The method according to claim 13,
wherein the emitting includes emitting at least three or more types of light including a first light in a first wavelength band, a second light in a second wavelength band that is different from the first wavelength band, and a third light in a third wavelength band that is different from the first wavelength band and the second wavelength band, and
wherein the generating a plurality of pieces of color image data includes generating first color image data corresponding to the first light, second color image data corresponding to the second light, and third color image data corresponding to the third light by imaging biological tissue illuminated with the first light, the second light, and the third light, respectively, and
wherein the first ratio is a ratio between one component of the first color image data and one component of the second color image data, and wherein the second ratio is a ratio between one component of the second color image data and one component of the third color image data.

15. The method according to claim 14,
wherein the first wavelength band is wider than the second wavelength band and the third wavelength band, and the second wavelength band is wider than the third wavelength band, and
wherein the first wavelength band includes a wavelength band according to which one component of the first color image data is not sensitive to change in the amount of hemoglobin of the biological tissue.

16. The method according to claim 14,
wherein the second wavelength band includes a wavelength band according to which one component of the second color image data is sensitive to change in the amount of hemoglobin of the biological tissue but is not sensitive to change in the oxygen saturation.

17. The method according to claim 14,
wherein the first ratio is a ratio between a luminance component of the second color image data and an R component of the first color image data or is a ratio between the luminance component of the second color image data and a sum of the R component and a G component of the first color image data.

18. The method according to claim 14,
wherein the second ratio is a ratio between a luminance component of the third color image data and a luminance component of the second color image data.

19. The method according to claim 14,
wherein the second wavelength band is in a range of 500 nm to 600 nm,
the third wavelength band is a wavelength band that is in the second wavelength band and is narrower than the second wavelength band, and
the second light is filtered light obtained from the first light by using an optical filter to transmit a light component in the second wavelength band, and the third light is filtered light obtained from the first light by using an optical filter to transmit a light component in the third wavelength band.

20. The method according to claim 14,
wherein the third wavelength band includes a wavelength band according to which one component of the third color image data is sensitive to change in the oxygen saturation.

* * * * *